United States Patent [19]

Katayama et al.

[11] Patent Number: 4,614,826
[45] Date of Patent: Sep. 30, 1986

[54] POLYGLYCIDYL ETHERS OF POLYNUCLEAR POLYHYDRIC PHENOLS

[75] Inventors: Shigeru Katayama, Ichihara; Takayuki Nakano, Ohtake; Nobuyuki Takeda, Chiba, all of Japan

[73] Assignee: Mitsui Petrochemical Industries, Ltd., Tokyo, Japan

[21] Appl. No.: 583,636

[22] Filed: Feb. 27, 1984

[30] Foreign Application Priority Data

Feb. 28, 1983 [JP] Japan ................................. 58-30759
Feb. 28, 1983 [JP] Japan ................................. 58-30761

[51] Int. Cl.$^4$ .................. C07D 303/26; C07D 303/27
[52] U.S. Cl. .................................... 549/559; 549/560; 549/517; 568/720; 525/523
[58] Field of Search .................. 568/720; 549/559, 560

[56] References Cited

U.S. PATENT DOCUMENTS 3,285,938 11/1966 Sellers .............................. 549/560
3,660,202 5/1972 Edington et al. .................... 568/720
4,163,801 8/1979 McGarry ........................... 425/347

FOREIGN PATENT DOCUMENTS 37-13869 9/1962 Japan .
58-13528 1/1983 Japan .
58-24531 2/1983 Japan .
58-18331 12/1983 Japan .

OTHER PUBLICATIONS

Tanaka et al., Kobunshi Kagaku, 20, 634–640 (1963).
Aelony, J. Applied Poly. Sci, IV(11), 141–150 (1960).

*Primary Examiner*—Norma S. Milestone
*Attorney, Agent, or Firm*—Wenderoth, Lind & Ponack

[57] ABSTRACT

Disclosed are a polynuclear polyhydric phenol represented by the following general formula [I]:

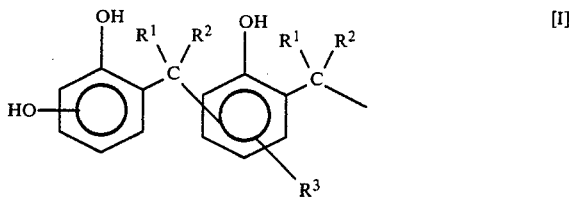

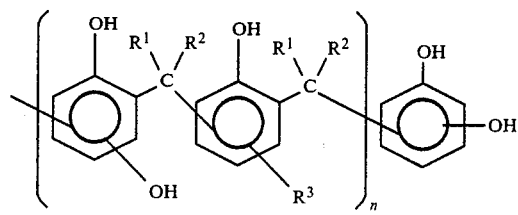

wherein $R^1$ and $R^2$ stand for a hydrogen atom or a lower alkyl group, $R^3$ stands for a hydrogen atom, an alkyl group, an aryl group or a halogen atom, and n is an integer of from 0 to 10, and a polyepoxy compound consisting of a polyglycidyl ether of this polynuclear polyhydric ether. When this polyepoxy compound is combined with a curing agent, a curable epoxy resin composition excellent in the heat resistance characteristics is provided.

4 Claims, No Drawings

POLYGLYCIDYL ETHERS OF POLYNUCLEAR POLYHYDRIC PHENOLS

BACKGROUND OF THE INVENTION (1) Field of the Invention:

The present invention relates to a novel polynuclear polyhydric phenol, a polyepoxy compound derived therefrom and a process for the preparation thereof. Furthermore, the present invention provides a curable epoxy resin composition having excellent heat resistance characteristics such as high glass transition point, high heat distortion temperature and high heat-resistant elastic property.

(2) Description of the Prior Art:

Various polyepoxy compounds have heretofore been proposed as components to be incorporated into curable epoxy resin compositions. In the fields of molding materials, varnishes, laminates for printed circuits, advanced composite materials and the like, curable epoxy resin compositions excellent in heat resistance characteristics such as glass transition point, heat distortion temperature and heat-resistant elastic property have recently been eagerly required. As the polyepoxy compound constituting a heat-resistant curable epoxy resin composition, there have been used epoxidized phenol-novolak resins, epoxidized o-cresol-novolak resins, polyglycidyl ethers of polynuclear polyhydric phenols such as 1,1,2,2-tetrakis(p-hydroxyphenyl)ethane tetraglycidyl ether, and polyglycidyl compounds of aromatic polyamines such as a tetraglycidyl compound of xylylene diamine, a hexaglycidyl compound of 1,3,5-triaminomethylbenzil and a triglycidyl compound of isocyanuric acid. However, curable epoxy resin compositions including these polyepoxy compounds are still insufficient in the above-mentioned heat resistance characteristics, and they cannot be used in the fields where high heat resistance characteristics are required. Therefore, development of curable epoxy resin compositions having improved heat resistance characteristics has been desired.

Many polynuclear polyhydric phenols are known in addition to the above-mentioned polynuclear polyhydric phenols. For example, there have been proposed polynuclear polyhydric phenols such as ω,ω'-bis(3,4-dihydroxyphenyl)xylene (Japanese Patent Publication No. 13869/62) 2,4-bis(2,4-dimethylbenzyl)-6-(2-hydroxybenzyl)phenol [Hiroshi Kakiuchi and Yoshio Tanaka; Polymer Chemistry, 20, 643 (1963)], 1,1,2,2-tetrakis(4-hydroxyphenyl)ethane and 1,1,5,5-tetrakis(4-hydroxyphenyl)pentane [D, Aelony; J. Applied Polymer Sci., 4, 141 (1960)], 1,3-bis(2-p-hydroxyphenyl-2-propyl)benzene (Japanese Patent Application Laid-Open Specification No. 13528/83), and 1,4-bis(2-p-hydroxyphenyl-2-propyl)benzene (Japanese Patent Application Laid-Open Specification No. 18331/83). However, even if polyglycidyl ethers of these compounds are used for curable epoxy resin compositions, the above-mentioned heat resistance characteristics are still insufficient, and the compositions cannot be used in the fields where high heat resistance characteristics are required.

SUMMARY OF THE INVENTION

We succeeded in synthesizing polynuclear polyhydric phenols not taught in literature references, which will be described in detail hereinafter. It was found that a curable epoxy resin composition comprising a polyepoxy compound consisting of a polyglycidyl ether of a member selected from these phenols is excellent in the heat resistance characteristics. Namely, curable epoxy resin compositions formed by incorporating curing agents into polyepoxy compounds consisting of polyglycidyl ethers of the above-mentioned polynuclear polyhydric phenols are especially excellent in heat resistance characteristics such as glass transition point, heat distortion temperature and heat-resistant elastic property and also in mechanical characteristics such as flexural strength, Izod impact strength and Rockwell hardness. Furthermore, the polynuclear polyhydric phenols of the present invention are effectively used as stabilizers such as heat-resistant stabilizers, weathering stabilizers and antioxidants and also as curing agents for epoxy resins.

In accordance with one fundamental aspect of the present invention, there is provided a polynuclear polyhydric phenol represented by the following general formula [I]:

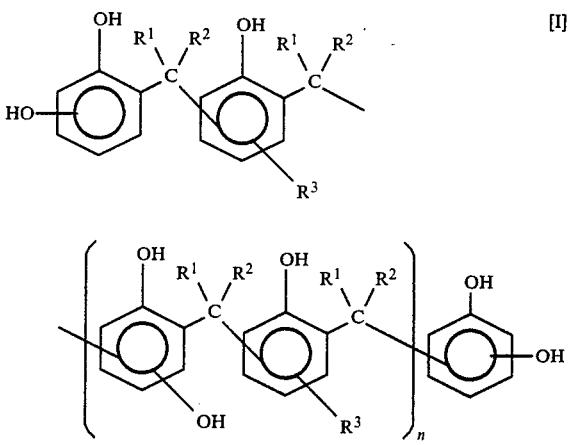

wherein $R^1$ and $R^2$ stand for a hydrogen atom or a lower alkyl group, $R^3$ stands for a hydrogen atom, an alkyl group, an aryl group or a halogen atom, and n is an integer of from 0 to 10.

In accordance with another fundamental aspect of the present invention, there is provided a process for the preparation of polynuclear polyhydric phenols represented by the following general formula [I]:

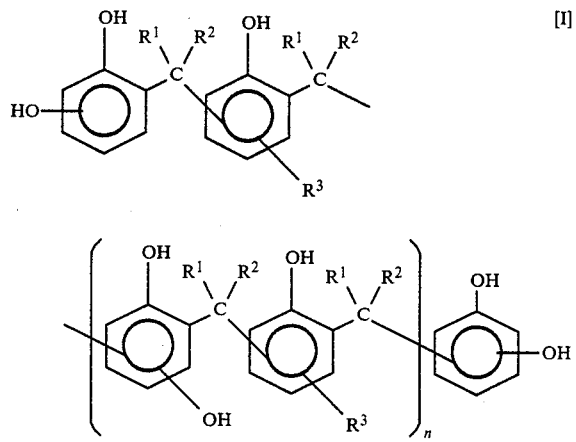

wherein $R^1$ and $R^2$ stand for a hydrogen atom or a lower alkyl group, $R^3$ stands for a hydrogen atom, an alkyl group, an aryl group or a halogen atom, and n is an integer of from 0 to 10, which comprises reacting a dihydric phenol with a substituted phenol represented by the following general formula [II]:

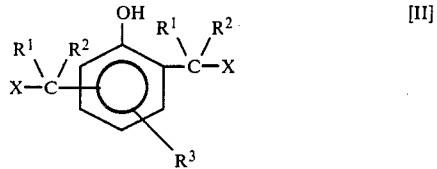

wherein $R^1$, $R^2$ and $R^3$ are as defined above, and X stands for a hydroxyl group or a halogen atom, in the presence of an acid catalyst.

DETAILED DESCRIPTION OF THE PREFERRED EMBODIMENTS

[Polynuclear Polyhydric Phenols and Process for Preparation Thereof]

The polynuclear polyhydric phenol of the present invention is a polynuclear polyhydric phenol represented by the following general formula [I]:

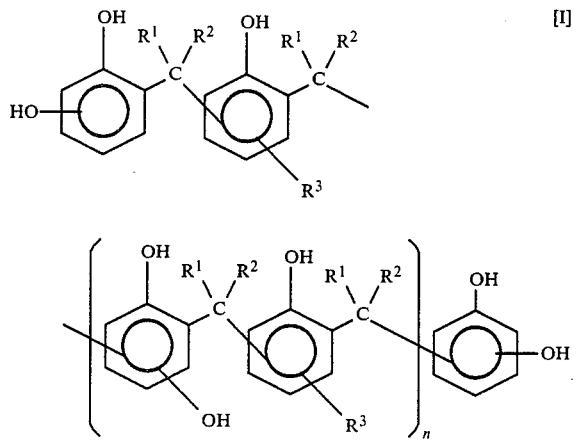

wherein $R^1$ and $R^2$ stand for a hydrogen atom or a lower alkyl group, $R^3$ stands for a hydrogen atom, an alkyl group, an aryl group or a halogen atom, and n is an integer of from 0 to 10.

As the dihydroxyphenyl group constituting the polynuclear polyhydric phenol represented by the general formula [I], there can be mentioned a 3,4-dihydroxyphenyl group, a 2,4-dihydroxyphenyl group and a 2,5-dihydroxyphenyl group, and as the dihydroxyphenylene group, there can be mentioned a 3,4-dihydroxy-1,6-phenylene group, a 2,4-dihydroxy-1,5-phenylene group and a 2,5-dihydroxy-1,3-phenylene group. These groups correspond to catechol component units, resorcinol component units and hydroquinone component units, respectively. At least two kinds of dihydroxyphenyl groups or at least two kinds of dihydroxyphenylene groups may be contained in one molecule of the polynuclear polyhydric phenol. As the groups $R^1$ and $R^2$ constituting the polynuclear polyhydric phenol represented by the general formula [I], there can be mentioned, for example, a hydrogen atom, and lower alkyl groups such as methyl, ethyl, propyl and butyl groups. It is preferred that at least one of $R^1$ and $R^2$ be a hydrogen atom. As the group $R^3$, there can be mentioned, for example, a hydrogen atom, alkyl groups such as methyl, ethyl, propyl, butyl, pentyl, hexyl, octyl, nonyl, decyl and dodecyl groups, aryl groups such as phenyl, tolyl and chlorophenyl groups, and halogen atoms such as fluorine, chlorine and bromine atoms. The group $R^3$ may be located at either the ortho-position or the para-position to the hydroxyl group. In the polynuclear polyhydric phenol represented by the general formula [I], n is an integer of from 0 to 10. A mixture of polynuclear polyhydric phenols in which n is an integer within the above-mentioned range is included within the scope of the present invention.

As examples of the polynuclear polyhydric phenol represented by the general formula [I], there can be mentioned, in the order of importance, polynuclear polyhydric phenols represented by the following general formulae [III] through [VIII]:

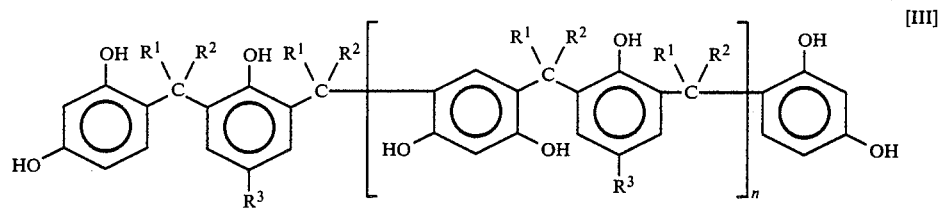

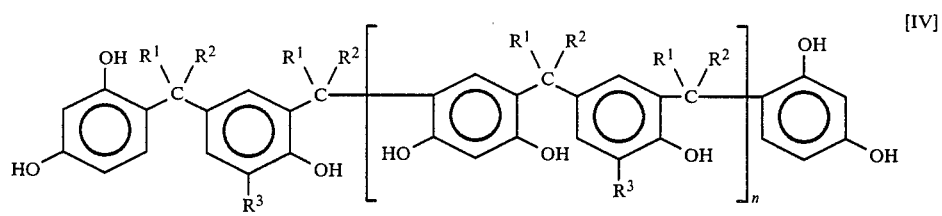

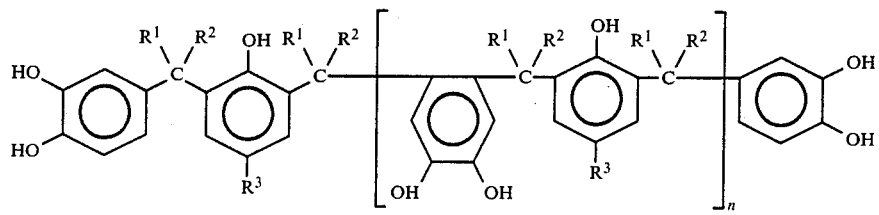
[V]

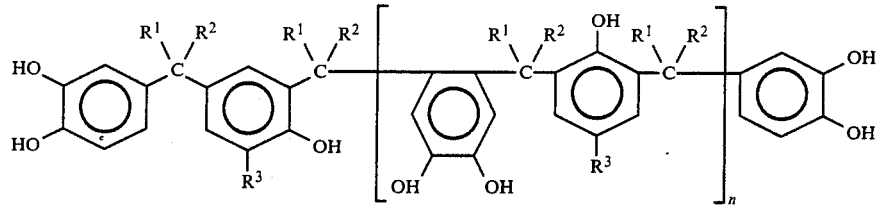
[VI]

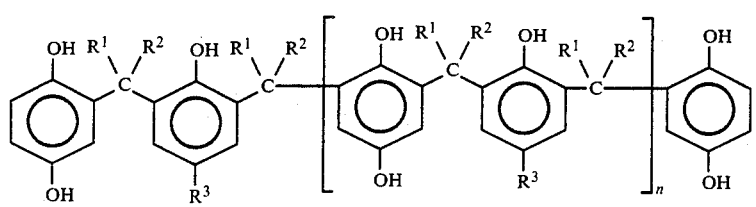
[VII]

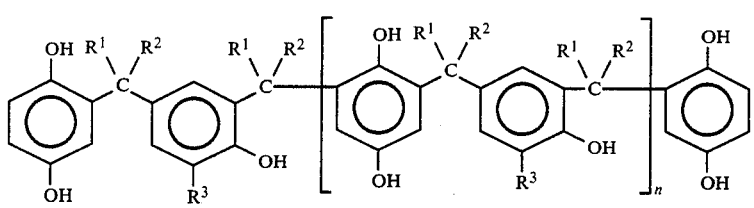
[VIII]

The polynuclear polyhydric phenol of the present invention can be prepared by reacting a dihydric phenol with a specific substituted phenol represented by the general formula [II] given below in the presence of an acid catalyst. As the dihydric phenol used as the starting substance in the process of the present invention, there can be mentioned mononuclear dihydric phenols such as catechol, resorcinol and hydroquinone. A mixture of two or more of these mononuclear dihydric phenols may also be used. The dihydric phenol is ordinarily used in an amount of 1 to 8 moles, preferably 2 to 4 moles, per mole of the substituted phenol described hereinafter.

The substituted phenol used in the process of the present invention is a substituted phenol represented by the following general formula [II]:

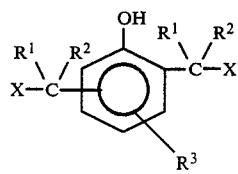
[II]

wherein $R^1$ and $R^2$ stand for a hydrogen atom or a lower alkyl group, $R^3$ stands for a hydrogen atom, an alkyl group, an aryl group or a halogen atom, and X stands for a hydroxyl group or a halogen atom.

As specific examples of the substituted phenol represented by the general formula [II], there can be mentioned 2,6-bis(hydroxymethyl)phenol, 2,4-bis(hydroxymethyl)-6-chlorophenol, 2,6-bis(hydroxymethyl)-p-cresol, 2,4-bis(hydroxymethyl)-o-cresol, 2,4-bis(hydroxymethyl)-6-ethylphenol, 2,6-bis(hydroxymethyl)-4-propylphenol, 2,4-bis(hydroxymethyl)-6-bromophenol, 2,6-bis(hydroxymethyl)-4-hexylphenol, 2,6-bis(hydroxymethyl)-4-octylphenol, 2,4-bis(hydroxymethyl)-6-decylphenol, 2,6-bis(hydroxymethyl)-4-dodecylphenol, 2,6-bis(hydroxymethyl)-4-phenylphenol, 2,6-bis(hydroxymethyl)-4-tolylphenol, 2,6-bis(hydroxymethyl)-4-(p-chlorophenyl)phenol, 2,4-bis(hydroxymethyl)-6-phenylphenol, 2,6-bis(hydroxymethyl)-6-phenylphenol, 2,6-bis(chloromethyl)phenol, 2,4-bis(bromomethyl)phenol, 2,6-bis(iodomethyl)-4-chlorophenol, 2,6-bis(chloromethyl)-p-cresol, 2,4-bis(chloromethyl)-o-cresol, 2,6-bis(chloromethyl)-4-ethylphenol, 2,4-bis(chloromethyl)-6-propylphenol, 2,6-bis(chloromethyl)-4-butylphenol, 2,6-bis(chloromethyl)-4-octylphenol, 2,6-bis(1-hydroxyethyl)phenol, 2,6-bis(1-hydroxyethyl)-p-cresol, 2,4-bis(1-hydroxyethyl)-o-cresol, 2,6-bis(1-hydroxyethyl)-6-octylphenol, 2,6-bis(1-hydroxypropyl)-p-cresol, 2,4-bis(1-hydroxypropyl)-o-cresol, 2,6-bis(1-hydroxypropyl)-4-dodecylphenol, 2,6-bis(1-hydroxybutyl)-4-isopropylphenol, 2,6-bis(1-hydroxybutyl)-4-isopropylphenol, 2,6-bis(1-hydroxy-2-chloroethyl)phenol, 2,6-(1-hydroxy-2-chloroethyl)-p-cresol, 2,6-bis(1-hydroxy-2,2-dichloroethyl)-p-cresol, 2,6-bis(1-hydroxy-2,2-dichloroethyl)-4-chlorophenol, 2,6-bis(1-dichloroethyl)-4-isopropylphenol, 2,6-bis(1-hydroxy-2,2,2-trichloroethyl)-p-cresol, 2,4-bis(1-hydroxy-2,2,2-trichloroethyl)-o- cresol, 2,6-bis(1-hydroxy-2,2,2-trichloroethyl)-4-bromophenol, 2,6-bis(1-chloroethyl)-p-cresol, 2,4-bis(1-bromoethyl)-o-cresol, 2,6-bis(1-bromopropyl)-p-cresol and 2,4-bis(1-chloropropyl)-6-chlorophenol.

As the acid catalyst used in the present invention, there can be mentioned protonic acids such as sulfuric acid, nitric acid, hydrochloric acid, perchloric acid, phosphoric acid, toluene-sulfonic acid and methane-sulfonic acid, and Lewis acids such as boron trifluoride, boron trifluoride complexes, e.g., a boron trifluorideether complex, aluminum trichloride, tin tetrachloride, zinc chloride, ferric chloride and titanium tetrachloride. Among these acids catalysts, protonic acids are preferred, and nitric acid, sulfuric acid, hydrochloric acid and p-toluene-sulfonic acid are especially preferred. The acid catalyst is ordinarily used in an amount of 0.1 to 10 parts by weight per 100 parts by weight of the substituted phenol represented by the general formula [II].

In the process of the present invention, the reaction is ordinarily carried out in the presence of a solvent, but the reaction can be carried out even in the absence of a solvent. In the case where the reaction is carried out in the absence of a solvent, the starting material mixture is heated at a temperature higher than the melting temperature and the molten mixture is stirred, and water or a hydrogen halide, formed by the reaction, is removed by distillation under atmospheric or deduced pressure. When the reaction is carried out in the presence of a solvent, toluene, o-dichlorobenzene, diphenyl ether, decalin, methanol or ethanol may be used as the solvent. The solvent is used in an amount of ordinarily 80 to 300 parts by weight, preferably 100 to 200 parts by weight, per 100 parts by weight of the sum of the amounts of the starting dihydric phenol and substituted phenol.

The reaction temperature is 40° to 120° C. and preferably 50° to 90° C. The reaction time is not particularly critical and is optionally changed according to the reaction temperature and other conditions. The reaction time is ordinarily 2 to 12 hours and preferably 4 to 8 hours. After completion of the reaction, the reaction mixture is poured into a poor solvent such as methanol, acetone or water to effect precipitation or the solvent is removed by distillation under heating, whereby the polynuclear polyhydric phenol of the present invention can be obtained.

In accordance with still another aspect of the present invention, there is provided a polyepoxy compound consisting of a polyglycidyl ether of a polynuclear polyhydric phenol represented by the above-mentioned general formula [I].

Furthermore, in accordance with the present invention, there is provided a process for the preparation of a polyepoxy compound consisting of a polyglycidyl ether of a polynuclear polyhydric phenol represented by the above-mentioned general formula [I], which comprises reacting a polynuclear polyhydric phenol represented by the above-mentioned general formula [I] with an epihalohydrin in the presence of a catalyst to form a halohydrin ether of the polynuclear polyhydric phenol and reacting said halohydrin ether with an alkali metal hydroxide.

[Polyepoxy Compound and Process for Preparation Thereof]

Examples of the polynuclear polyhydric phenol used for the production of the polyepoxy compound of the present invention are polynuclear polyhydric phenols described hereinafter.

The polyepoxy compound of the present invention is a polyglycidyl ether of the polynuclear polyhydric phenol represented by the above-mentioned general formula [I], and in this polyepoxy compound, at least 80%, preferably at least 90%, especially preferably at least 95%, of the phenolic hydroxyl groups of the polynuclear polyhydric phenol are glycidyl-etherified. By the term "glycidyl ether" used herein are meant a glycidyl ether represented by the following formula [IX]:

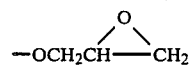  [IX]

which is formed by reaction between one phenolic hydroxyl group of the polynuclear polyhydric phenol and one molecule of the epihalohydrin, and a mixture of this glycidyl ether and 2-hydroxy-1,3-propylene diether represented by the following formula [X]:

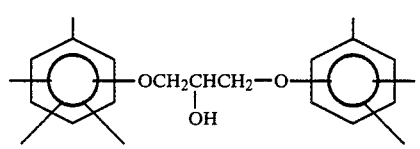  [X]

which is obtained by reaction between the phenolic hydroxyl group and the formed glycidyl ether. In the polyepoxy compound of the present invention, the molar ratio of the above-mentioned 2-hydroxy-1,3-propylene diether group to the total glycidyl groups is ordinarily up to 0.5 and preferably up to 0.1. The epoxy equivalent of the polyepoxy compound of the present invention is ordinarily 122 to 500 g/equivalent and preferably 125 to 400 g/equivalent, and the phenolic hydroxyl equivalent is ordinarily at least 1220 g/equivalent and preferably at least 2500 g/equivalent.

The polyepoxy compound of the present invention is prepared by reacting the polynuclear polyhydric phenol represented by the general formula [I] with an epihalohydrin in the presence of a catalyst to form a halohydrin ether of the polynuclear polyhydric phenol and reacting said halohydrin ether with an alkali metal hydroxide. As the epihalohydrin used in the process of the present invention, there can be mentioned, for example, epichlohydrin, epibromohydrin and epiiodohydrin. The epihalohydrin is used in an amount of 1 to 15 moles, preferably 3 to 7 moles, per mole of the phenolic hydroxyl group of the polynuclear polyhydric phenol.

A base or an ammonium salt may be used as the catalyst in the process of the invention of this application. As typical examples, there can be mentioned alkali metal hydroxides such as sodium hydroxide, potassium hydroxide and lithium hydroxide, primary amines such as propylamine, butylamine, hexylamine and octylamine, secondary amines such as diethylamine, dipropylamine and dibutylamine, tertiary amines such as triethylamine, tripropylamine and tributylamine, quaternary ammonium salts such as tetramethyl ammonium chloride, tetramethyl ammonium bromide, tetraethyl ammonium chloride, tetraethyl ammonium bromide, tetraethyl ammonium iodide, tetrapropyl ammonium chloride, tetrabutyl ammonium chloride, benzyltrimethyl ammonium chloride, benzyltrimethyl ammonium bromide, benzyltrimethyl ammonium iodide and chlorine chloride, and amine salts such as trimethylamine hydrochloride, triethylamine hydrochloride, dimethylamine hydrobromide and diethylamine hydrochloride. The catalyst is used in an amount of 0.005 to 5 moles, preferably 0.01 to 1 mole, per mole of the polynuclear polyhydric phenol.

In the process of the present invention, the halohydrin ether-forming reaction is carried out at a temperature of 50° to 110° C., preferably 70° to 100° C. At this halohydrin ether-forming reaction step, there may be adopted a method in which the phenolic hydroxy groups of the polynuclear polyhydric phenol are substantially completely converted to halohydrin ether groups. Furthermore, there may be adopted a method in which the phenolic hydroxyl groups of the polynuclear polyhydric phenol are converted to halohydrin ether groups only partially, for example, at a ratio of 40 to 80%, preferably 50 to 70%, to obtain a mixture of a halohydrin ether of the polynuclear polyhydric phenol and the starting materials and this mixture is reacted with an alkali metal hydroxide to simultaneously advance the halohydrin ether-forming reaction and the dehydrohalogenation reaction.

In the process of the present invention, the dehydrohalogenation reaction of the halohydrin ether is carried out in the presence of an alkali metal hydroxide. As the alkali metal hydroxide, there can be mentioned, for example, sodium hydroxide, potassium hydroxide and lithium hydroxide. Use of sodium hydroxide is preferred. The alkali metal hydroxide is used in an amount of 0.80 to 1.2 moles, preferably 0.95 to 1.1 moles, per mole of the phenolic hydroxyl group of the starting polynuclear polyhydric phenol supplied to the halohydrin ether-forming reaction step. The dehydrohalogenation reaction of the halohydrin ether is preferably carried out while removing water formed by the reaction from the reaction system. As means for removing water, there can be mentioned, for example, a method in which formed water is removed by azeotropic distillation with the epihalohydrin in the reaction system, the distillate is separated into an aqueous phase and an epihalohydrin phase and the epihalohydrin phase is circulated to the reaction system. The dehydrohalogenation reaction may be carried out in one stage or in two or multiple stages. The dehydrohalogenation reaction is ordinarilly carried out in the presence as the solvent of the epihalohydrin used as the starting compound at the halohydrin ether-forming reaction. Alternately, the dehydrohalogenation reaction may be carried out in a keytone solvent such as methylethyl ketone or methylisobutyl ketone or an aromatic hydrocarbon solvent such as benzene, toluene, xylene, cumene, cymene or ethylbenzene. The solvent is used in an amount 4 to 10 times, preferably 5 to 7 times, the amount of the starting polynuclear polyhydric phenol on the weight basis. The dehydrohalogenation reaction is ordinarily carried out at a temperature of 70° to 110° C., preferably 80° to 100° C.

In the process of the present invention, the polyglycidyl ether of the polynuclear polyhydric phenol is separated from the reaction mixture obtained through the above-mentioned dehydrohalogenation reaction. This separation can be accomplished according to customary procedures. For example, the polyglycidyl ether of the polynuclear polyhydric phenol is obtained by neutralizing the unreacted alkali metal hydroxide in the reaction mixture with an aqueous solution of phosphoric acid, an alkali metal phosphate or acetic acid, removing the formed salt by extraction, adsorption or filtration and removing the solvent by distillation.

In accordance with still another aspect of the present invention, there is provided a curable epoxy resin composition comprising (a) a polyepoxy compound consisting of a polyglycidyl ether of a polynuclear polyhydric phenol represented by the above-mentioned general formula [I] and (b) a curing agent.

[Epoxy Resin Composition]

As the polyepoxy compound (a), there can be used polyepoxy compounds exemplified hereinabefore.

Namely, the polyepoxy compound of the present invention can be used in the form of a curable epoxy resin composition formed by incorporating a curing agent into the polyepoxy compound. All of compounds that are known as curing agents for epoxy resins can be used in the present invention. For example, there can be mentioned linear aliphatic polyamines such as diethylene triamine, triethylene tetraamine, tetraethylene pentamine, dipropylene diamine and diethylaminopropylamine, cyclic aliphatic polyamines such as menthane diamine, N-aminoethylpiperazine, isophorone diamine and 1,3-diaminocyclohexane, aliphatic polyamine adducts such as a diethylene triamin/ethylene oxide adduct and a diethylene triamine/propylene oxide adduct, ketoimines such as a diethylene triamine/acetone condensate, modified aliphatic polyamines such as cyanoethylated diethylene triamine, polyamine-amines such as a dimer acid/diethylene triamine condensate and a dimer acid/triethylene tetraamine condensate, aromatic amines such as 4,4'-methylene-dianiline, m-phenylenediamine and xylylenediamine, aromatic modified amines such as a 4,4'-methylene-dianiline/phenylglycidyl ether adduct, mercaptan type curing agents such as a polysulfide resin, acid anhydride type curing agents such as hexahydrophthalic anhydride, methyltetrahydrophthalic anhydride, phthalic anhydride and tetrabromophthalic anhydride, acid anhydride group-containing copolymers such as an ethylene/maleic anhydride copolymer, phenolic hydroxy group-containing compounds such as a novolak type phenolic resin precondensate and a resol type phenolic resin precondensate, dicyandiaminde, an aniline/formaldehyde resin, a melamine resin, and a urea resin. An appropriate curing agent is preferably selected and used according to the intended use of the composition. The curing agent is ordinarily incorporated in an amount of 1 to 200 parts by weight, preferably 3 to 100 parts by weight, per 100 parts by weight of the polyepoxy compound.

In addition to the above-mentioned polyepoxy compound and curing agent, various additives such as a curing promotor, an inorganic or organic filler, a flame retardant, a heat-resistant stabilizer, an antioxidant, a lubricant and a diluent may be incorporated into the curable epoxy resin composition of the present invention according to need. Furthermore, a known polyepoxy compound may be used as a diluent in combination with the polyepoxy compound of the present invention.

A known curing promoter maybe used as the curing promotor in the present invention. For example, there can be mentioned benzyldimethylamine, 2-(dimethylaminomethyl)phenol, 2,4,6-tris(dimethylaminomethyl)phenol, N,N'-dimethylpiperazine and 2-ethyl-4-methylimidazole. The curing promotor is ordinarily used in an amount of 0.1 to 10 parts by weight, preferably 1 to 5 parts by weight, per 100 parts by weight of the polyepoxy compound.

As typical examples of the inorganic filler, there can be mentioned silica, silica-alumina, alumina, glass powder, glass bead, glass fiber, asbestos, mica, graphite, carbon filter, titanium oxide, molybdenum disulfide, beryllium oxide, magnesium oxide, calcium oxide, magnesium hydroxide, calcium hydroxide, talc, celite, metal powder and metal fiber. If any of these inorganic fillers is incorporated, the heat resistance characteristics and mechanical properties can be improved. Among these inorganic fillers, glass fiber, carbon fiber and asbestos are especially effective for improving the heat resistance characteristics. When graphite, titanium oxide or molybdenum disulfide is incorporated, the abrasion resistance is highly improved, and when mica, asbestos or glass fiber is incorporated, the arc resistance is highly improved. Furthermore, when carbon black, metal fiber, metal powder or graphite is incorporated, the electric properties such as the electric conductivity are improved, and when alumina, titanium oxide or beryllium oxide is incorporated, the heat conductivity is improved. The amount incorporated of the inorganic filler is changed according to the kind of the inorganic filler and the intended use of the curable epoxy resin composition. However, the inorganic filler is ordinarily incorporated in an amount of 10 to 250 parts by weight, preferably 30 to 200 parts by weight, especially preferably 60 to 150 parts by weight, per 100 parts by weight of the polyepoxy compound.

Various high polymers and fibrous polymers may be used as the organic filler. A fluorine type polymer such as polytetrafluoroethylene can be mentioned as the high polymer. As the fibrous organic filler, there can be mentioned polycondensate type synthetic fibers such as fibers of polyamides such as wholly aromatic polyamides, e.g., polyterephthaloyl-p-phenylene-diamine, polyterephthaloylisophthaloyl-p-phenylene-diamine, polyisophthaloyl-p-phenylene-diamine and polyisophthaloyl-m-phenylene-diamine, nylon 66, nylon 10 and nylon 12, polyamide-imide fibers, polybenzimidazole fibers and fibers of polyesters, e.g., polyethylene terephthalate and poly-1,4-butylene terephthalate, addition polymer type synthetic fibers such as polyvinyl alcohol type synthetic fibers and fibers of acrylic polymers, e.g., polyacrylonitrile, and natural fibers such as cotton fibers, hemp fibers, flax fibers, wool fibers and silk fibers. Among these fibrous organic fillers, a filler composed of polycondensate type synthetic fibers, especially a fibrous filler composed of a wholly aromatic polyamide, is preferred. The fibrous organic filler may be used in the form of a monofilament, a strand or a cloth. The size of the fiber of the fibrous organic filler is 3 to 20 microns, preferably 5 to 15 microns. The fiber may be a staple or filament. The fiber length is optionally selected according to the intended use, and the fiber length is ordinarily 0.1 to 1.2 cm and preferably 0.3 to 0.6 cm. The fibrous organic filler is incorporated in an amount of 1 to 60 parts by weight, preferably 5 to 40 parts by weight, especially preferably 10 to 30 parts by weight, per 100 parts by weight of the polyepoxy compound. In the case where the inorganic or organic filler is in the form of a cloth or mat, there may be adopted a method in which the curable epoxy resin composition is dissolved in an organic solvent to form a varnish, the cloth or mat substrate is impregnated with the varnish to form a prepreg, a plurality of such prepregs are piled according to need and molding is performed by press-curing, whereby a laminate composed of the composition of the present invention can be obtained. In the case where the inorganic or organic filler is in the form of a monofilament or strand, the filler may be incorporated according to a known method.

As typical examples of the flame retardant, there can be mentioned organic halogen compounds such as halogenated aliphatic hydrocarbons, halogenated alicyclic hydrocarbons, halogenated aromatic hydrocarbons, halogenated aromatic ethers, halogenated phenols, halogenated polynuclear polyhydric phenols, halogenated aromatic carboxylic acids, anhydrides thereof, halogenated novolak type phenolic resins and halogenated epoxynovolak type phenolic resins, boron compounds, phosphorus compounds such as inorganic and organic phosphorus compounds, antimony compounds such as inorganic and organic antimony compounds, bismuth compounds, and arsenic compounds. The flame retardant is incorporated in an amount of 1 to 100 parts by weight, preferably 3 to 50 parts by weight, per 100 parts by weight of the polyepoxy compound.

The curable epoxy resin composition of the present invention is especially excellent in heat resistance characteristics such as glass transition point, heat distortion temperature and heat-resistant elastic property and also excellent in mechanical properties such as flexural strength, Izod impact strength and Rockwell hardness. Because of these excellent characteristics, the curable epoxy resin composition of the present invention can be widely used in various fields. For example, the composition of the present invention is used as an adhesive, a varnish, a paint, an insulating material, a prepreg, a construction laminate, a laminate for a printed circuit, a distributing panel, a sealant for a transistor, IC or LSI, a molding material for electric appliances such as a switch and a connector and a molding material for sliding members such as a washer and a bearing.

The present invention will now be described in detail with reference to the following Examples that by no means limit the scope of the invention.

EXAMPLE 1

A reaction vessel was charged with 1980 g (18 moles) of resorcinol, 504 g (3 moles) of 2,6-dimethylol-p-cresol, 9 g (0.05 mole) of p-toluene-sulfonic acid and 4500 g of ethanol, and reaction was carried out for 4 hours under reflux. Under a reduced pressure of 300 mmHg, ethanol was removed and the reaction mixture was concentrated. The content in the reaction vessel was poured into 26 liters of water to precipitate a reaction product. The product was recovered by filtration, washed with water and dried to obtain 740 g of a resin.

The melting point of the resin was 128° to 135° C. as determined according to the microscope method, and the number average molecular weight $\overline{Mn}$ of the resin was 360 as determined by gel permeation chromatography. In the IR spectrum of this compound, characteristic absorptions of the phenolic —OH group, the aromatic nucleus and the methyl group were observed at about 3500 cm$^{-1}$, about 1600 and 1500 cm$^{-1}$ and about 1450 cm$^{-1}$, respectively. The resin was dissolved in dimethylsulfoxide-d$_6$ and the $^1$H nuclear magnetic resonance spectrum analysis was carried out. The obtained results are shown in Table 1.

TABLE 1

| δ(ppm, TMS standard) | Assignment | Relative Intensity |
|---|---|---|
| 2.04 | —CH₃ | 3 |
| 3.64 | —CH₂— | 4 |
| 6.76–6.08 | 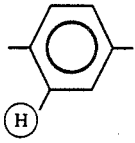 | 8 |
| 8.0 | 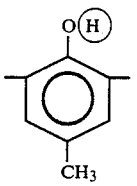 | 1 |
| 8.6, 9.36 | 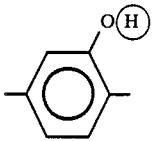 | 2 |

From the foregoing results, it was confirmed that the resin had the following structure:

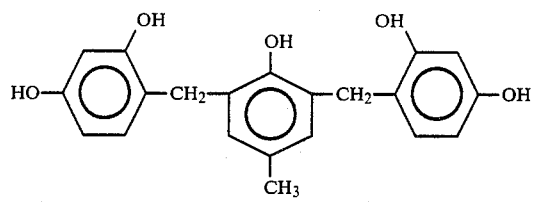

EXAMPLE 2

The procedures of Example 1 were repeated in the same manner except that 1512 g (9 moles) of 2,6-dimethylol-p-cresol was used, to obtain 2750 g of a resin.

The melting point of the resin was 157° to 172° C. as determined by the microscope method, and the number average molecular weight $\overline{Mn}$ determined by gel permeation chromatography was 900, the polymerization degree n was 2 and the molecular weight distribution $\overline{Mw}/\overline{Mn}$ was 1.42.

The resin was dissolved in dimethylsulfoxide-d₆ and the ¹H nuclear magnetic resonance spectrum analysis was carried out. The obtained spectrum was the same as that obtained in Example 1 except that the line widths of the peaks were broadened.

From the foregoing results, it was confirmed that the resin had the following structure:

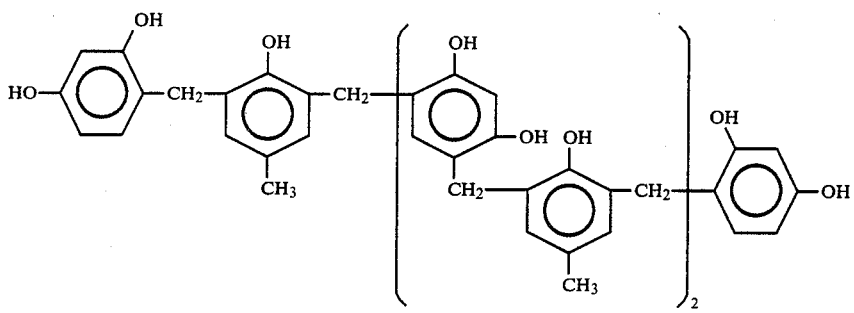

EXAMPLES 3 AND 4

The procedures of Example 1 were repeated in the same manner except that hydroquinone or catechol was used instead of resorcinol. The obtained results are shown in Table 2.

The structures of the obtained resins were analyzed in the same manner as described in Example 1. It was found that the resins had a structure in which hydroquinone or catechol was bonded to the p-cresol skelton through the methylene group.

TABLE 2

| Example No. | Dihydric Phenol | Amount (g) and Yield % of Resin | Formed Resin |||
|---|---|---|---|---|---|
| | | | $\overline{Mn}$ | n | Melting Point (°C.) |
| 3 | hydroquinone | 988 (93) | 365 | 0 | 165–170 |
| 4 | catechol | 850 (80) | 370 | 0 | (semi-solid) |

EXAMPLES 5 THROUGH 8

The procedures of Example 2 were repeated in the same manner as described in Example 2 except that 2,6-dimethylol-p-tert-butylphenol, 2,6-dimethylol-p-chlorophenol, 2,6-dimethylolphenol or 2,6-dimethylol-p-phenylphenol was used instead of 2,6-dimethylol-p-cresol as shown in Table 3. The obtained results are shown in Table 3.

The structures of the obtained resins were analyzed in the same manner as described in Example 2. It was found that the resins had a linear structure in which resorcinol units were alternately bonded to the p-tert-butylphenol, p-chlorophenol or phenol skeletons through methylene groups.

TABLE 3

| Example No. | Dimethylol Compound | Amount (g) Used | Amount (g) and Yield (%) of Resin | Formed Resin |||
|---|---|---|---|---|---|---|
| | | | | $\overline{Mn}$ | Polymerization Degree n | Melting Point (°C.) |
| 5 | 2,6-dimethylol-p-tert-butylphenol | 1800 | 2709 (76) | 960 | 2 | 150–165 |
| 6 | 2,6-dimethylol-p-chlorophenol | 1697 | 2360 (70) | 810 | 2 | 175–190 |

TABLE 3-continued

| Example No. | Dimethylol Compound | Amount (g) Used | Amount (g) and Yield (%) of Resin | Formed Resin | | |
|---|---|---|---|---|---|---|
| | | | | $\overline{Mn}$ | Polymerization Degree n | Melting Point (°C.) |
| 7 | 2,6-dimethylolphenol | 1386 | 2234 (73) | 600 | 1 | 140–155 |
| 8 | 2,6-dimethylol-p-phenylphenol | 2070 | 2608 (70) | 1000 | 2 | 200–215 |

EXAMPLE 9

The procedures of Example 2 were repeated in the same manner except that 2241 g (9 moles) of 2,6-di(1-chloropropyl)-4-methylphenol was used instead of 2,6-dimethylol-p-cresol, to obtain 3000 g of a resin. From the results of gel permeation chromatography, it was found that the number average molecular weight $\overline{Mn}$ was 1000, the polymerization degree n was 2 and the molecular weight distribution $\overline{Mw}/\overline{Mn}$ was 1.40.

The structure of the resin was analyzed in the same manner as described in Example 1. It was confirmed that the resin had a structure in which resorcinol was bonded to p-cresol through the isopropylidene group.

EXAMPLE 10

A reaction vessel was charged with 615 g (1.7 moles) of the resin obtained according to the method shown in Example 1, 4023 g (43.5 g) of epichlorohydrin, 57.2 g (0.26 mole) of a 50% aqueous solution of tetramethyl ammonium chloride and 64 g of water, and reaction was carried out with stirring at 90° C. for 4 hours.

Then, 798 g (9.6 moles) of a 48% aqueous solution of sodium hydroxide was added dropwise to the reaction mixture over a period of 1.5 hours. During this dropwise addition, the condensed distillate was separated, and the upper aqueous layer was removed and the lower epichlorohydrin layer was returned to the reaction vessel, so that the water concentration in the reaction mixture was maintained at about 2%.

After completion of the reaction, the reaction mixture was thrown into 2250 liters of water and the mixture was sufficiently stirred to wash the organic layer. Then, the organic layer was separated and 2250 liters of water was added thereto, and the mixture was sufficiently stirred to wash the organic layer. Then, the organic layer was separated and 240 ml of a 17% aqueous solution of sodium phosphate was added to effect neutralization. Water was removed from the organic layer by heating and the organic layer was then filtered. The filtrate was concentrated to obtain 960 g of an epoxy resin.

From the results of gel permeation chromatography, it was found that the number average molecular weight $\overline{Mn}$ was 1120 and the molecular weight distribution $\overline{Mw}/\overline{Mn}$ was 1.42. The resin had a melting point of 53° to 58° C. as determined by the microscope method, and the epoxy equivalent of the resin was 150 g/eq as determined by the hydrochloric acid-dioxane method.

In the IR spectrum of this resin, the characteristic absorptions of the phenyl and methyl groups shown in Example 1 were observed but the absorption of the phenolic —OH group at about 3500 cm$^{-1}$ disappeared, and new characteristic absorptions of the epoxy group were observed at about 840 cm$^{-1}$ and about 900 cm$^{-1}$. Thus, it was confirmed that the resin obtained in Example 1 was converted to a glycidyl ether in this Example.

The resin was dissolved in CDCl$_3$, and the nuclear magnetic resonance spectrum analysis was carried out. The obtained results are shown in Table 4. From these results, it was confirmed that the resin had the following structure:

TABLE 4

[Structural formula showing epoxidized resin with labeled positions a, b, c, d, e]

| δ(ppm, TMS Standard) | Assignment |
|---|---|
| 2.12 | a |
| 2.80 | b |
| 3.28 | c |
| 3.92 | d |
| 6.48–7.0 | e |

EXAMPLES 11 THROUGH 15

The procedures of Example 10 were repeated in the same manner except that the resin obtained in Example 2, 5, 6, 7 or 8 was used as shown in Table 5.

The physical properties of the obtained resin were measured according to the methods described in Example 10, and the obtained results are shown in Table 5.

From the IR spectra of these resins and the $^1$H nuclear magnetic resonance spectra of these resins dissolved in dimethylsulfoxide-d$_6$, it was found the resins had an epoxidized structure in which resorcinol units were alternately bonded to p-cresol, p-tert-butylphenol, p-chlorophenol, phenol or p-phenylphenol skeletons through methylene groups.

TABLE 5

| Example No. | Starting Resin | Amount (g) used | Amount (g) and Yield (%) of Resin | Formed Resin | | | |
|---|---|---|---|---|---|---|---|
| | | | | Mn | Mw/Mn | Melting Point (°C.) | Epoxy Equivalent (g/eq) |
| 11 | resin of Example 2 | 615 | 909 (82) | 1180 | 2.30 | 70–75 | 150 |
| 12 | resin of Example 5 | 673 | 1117 (97) | 1020 | 1.72 | 55–60 | 159 |
| 13 | resin of Example 6 | 637 | 1022 (91) | 970 | 1.92 | 50–55 | 158 |
| 14 | resin of Example 7 | 578 | 920 (90) | 830 | 1.76 | 50–60 | 150 |
| 15 | resin of Example 8 | 706 | 1039 (90) | 1450 | 1.65 | 100–120 | 150 |

EXAMPLES 16 AND 17

The procedures of Example 10 were repeated in the same manner except that the resin obtained in Example 3 or 4 was used. The properties of the obtained resins were determined according to the methods described in Example 10. The obtained results are shown in Table 6.

From the IR spectra of these resins and the $^1$H nuclear magnetic resonance spectra of the resins dissolved in dimethylsulfoxide-$d_6$, it was found that the resins had an epoxidized structure in which hydroquinone or catechol was bonded to the p-cresol skeleton through the methylene group.

TABLE 6

| Example No. | Starting Resin | Amount (g) and Yield (%) of Resin | Formed Resin | | | |
|---|---|---|---|---|---|---|
| | | | Mn | Mw/Mn | Melting Point (°C.) | Epoxy Equivalent (g/eq) |
| 16 | resin of Example 3 | 479 (80) | 1200 | 1.54 | 68–72 | 150 |
| 17 | resin of Example 4 | 485 (81) | 1240 | 1.65 | 48–53 | 162 |

EXAMPLE 18

The procedures of Example 10 were repeated in the same manner except that the resin obtained in Example 9 was used. The properties of the obtained resin were determined according to the methods described in Example 10. It was found that the number average molecular weight $\overline{Mn}$ was 1300, the molecular weight distribution $\overline{Mw}/\overline{Mn}$ was 1.50, the melting point was 80° to 85° C. and the epoxy equivalent was 180 g/eq.

EXAMPLE 19 AND COMPARATIVE EXAMPLE 1

At 80° C., 150 g of the resin obtained in Example 10 was melt-mixed with 49.5 g of diaminodiphenylmethane, and the mixture was subjected to cast molding. The molded product was heated and cured at 100° C. for 2 hours and at 150° C. for 4 hours. The physical properties of the obtained molded product (Example 19) were measured to obtain results shown in Table 7.

The above procedures were repeated in the same manner except that 190 g of a commercially available bisphenol A type epoxy resin (EPOMIK R-140 supplied by Mitsui Sekiyu Kagaku Epoxy K.K.). The physical properties of the obtained molded product (Comparative Example 19) were measured to obtain results shown in Table 7.

TABLE 7

| Items | Example 19 | Comparative Example 1 |
|---|---|---|
| Flexural Strength (Kg/mm$^2$) | 6.3 | 11.2 |
| Flexural Modulus ($\times 10^3$ Kg/mm$^2$) | 0.29 | 0.26 |
| Rockwell Hardness (M) | 121 | 102 |
| Glass Transition Temperature (°C.) | 330 | 163 |
| Heat Distortion Temperature (°C.) | 277 | 158 |

EXAMPLES 20 THROUGH 27

The procedures of Example 19 were repeated in the same manner except that the resins obtained in Examples 11 through 18 were used as shown in Table 8. The physical properties of the obtained molded products were measured. The obtained results are shown in Table 8.

TABLE 8

| Example No. | Epoxy Resin | Amount (g) | Flexural Strength (Kg/mm$^2$) | Flexural Modulus ($\times 10^3$ Kg/mm$^2$) | Rockwell Hardness (M) | Glass Transition Temperature (°C.) | Heat Distortion Temperature (°C.) |
|---|---|---|---|---|---|---|---|
| 20 | resin of Example 11 | 150 | 6.3 | 0.32 | 121 | 327 | 286 |
| 21 | resin of Example 12 | 159 | 3.7 | 0.28 | 120 | 332 | 288 |
| 22 | resin of Example 13 | 158 | 3.9 | 0.28 | 120 | 320 | 275 |
| 23 | resin of Example 14 | 150 | 6.5 | 0.33 | 120 | 300 | 265 |

TABLE 8-continued

| Example No. | Epoxy Resin | Amount (g) | Flexural Strength (Kg/mm²) | Flexural Modulus (× 10³ Kg/mm²) | Rockwell Hardness (M) | Glass Transition Temperature (°C.) | Heat Distortion Temperature (°C.) |
|---|---|---|---|---|---|---|---|
| 24 | resin of Example 15 | 150 | 7.0 | 0.29 | 118 | 310 | 273 |
| 25 | resin of Example 16 | 150 | 8.4 | 0.29 | 110 | 230 | 200 |
| 26 | resin of Example 17 | 162 | 7.3 | 0.28 | 120 | 330 | 289 |
| 27 | resin of Example 18 | 180 | 8.5 | 0.30 | 115 | 330 | 288 |

COMPARATIVE EXAMPLES 2 THROUGH 4

The procedures of Example 19 were repeated in the same manner except that commercially available heat-resistant epoxy resins were used as shown in Table 9. The physical properties of the obtained molded products were measured. The obtained results are shown in Table 9.

TABLE 9

| Comparative Example No. | Epoxy Resin | Amount (g) | Flexural Strength (Kg/mm²) | Flexural Modulus (×10³ Kg /mm²) | Rockwell Hardness (M) | Glass Transition Temperature (°C.) | Heat Distortion Temperature (°C.) |
|---|---|---|---|---|---|---|---|
| 2 | 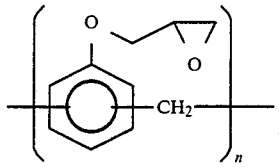 (EPPN-201 supplied by Nippon Kayaku) | 196 | 9.2 | 0.28 | 109 | 210 | 178 |
| 3 | 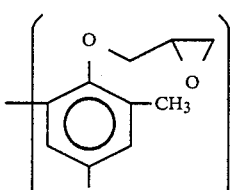 (ECON103 supplied by Nippon Kayaku) | 218 | 8.7 | 0.29 | 114 | 205 | 174 |
| 4 | 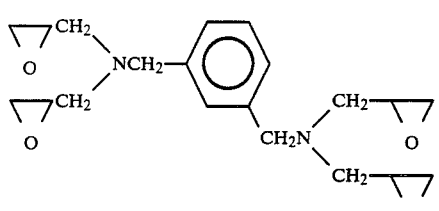 (TETRAD-X supplied by Mitsubishi Gas Kagaku) | 164 | 12.0 | 0.40 | 120 | 162 | 155 |

EXAMPLE 28 AND COMPARATIVE EXAMPLE 5

A varnish was prepared by dissolving 688 g of the resin obtained in Example 11, 37 g of dicyandiamide and 2.1 g of benzyldimethylamine in 373 g of dimethylformamide. A glass cloth (WE-18K-BZ-2 supplied by Nittobo) was impregnated with this varnish and dried at 140° C. for 4 minutes to form a prepreg. Nine sheets of the so-prepared prepregs were piled and two copper foils were placed on the top and bottom surfaces, respectively, and the assembly was press-formed at 170° C. for 1 hour. The physical properties of the obtained laminate (Example 28) were shown in Table 10.

A varnish was prepared by dissolving 80 g of a bisphenol A type epoxy resin (EPOMIK R-301 supplied by Mitsui Sekiyu Kagaku Epoxy) and 20 g of a bisphenol A type epoxy resin (EPOMIK R-140 supplied by Mitsui Sekiyu Kagaku Epoxy) in 20 g of methylethyl ketone and mixing the resulting solution with a solution of 4 g of dicyandiamide in 15 g of dimethylformamide and a solution of 0.2 g of benzyldimethylamine in 15 g of methyl cellosolve. The above procedures were repeated in the same manner except that the glass cloth was impregnated with the so-prepared varnish and a prepreg was prepared by drying the impregnated glass cloth at 130° C. for 8 minutes. The physical properties of the obtained laminate (Comparative Example 5) are shown in Table 10.

TABLE 10

| Items | Example 28 | Comparative Example 5 |
|---|---|---|
| Flexural Strength 23° C. (Kg/mm²) | 41.8 | 50.7 |
| 150° C. (Kg/mm²) | 34.9 | 8.4 |
| Flexural Modulus 23° C. (× 10³ Kg/mm²) | 2.04 | 2.07 |
| 150° C. (× 10³ Kg/mm²) | 2.00 | 0.54 |
| Glass Transition Temperature (°C.) | 310 | 132 |
| Copper Foil Peel Strength (Kg/cm) | 1.2 | 2.3 |

We claim:

1. A polyepoxy compound which is represented by the following formula:

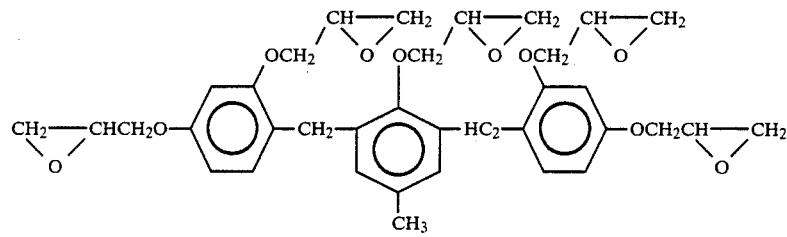

2. A polyepoxy compound consisting of a polyglycidyl ether of a polyhydric phenol of the formula:

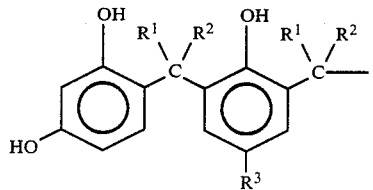

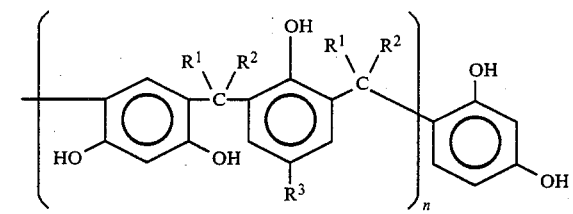

wherein $R^1$ and $R^2$ represent a hydrogen atom, $R^3$ represents $CH_3$, t—$C_4H_9$ or Cl, and n is 0 or 2, and wherein at least 80% of the phenolic hydroxyl groups are converted to glycidyl ether groups.

3. A polyepoxy compound consisting of a polyglycidyl ether of a polyhydric phenol of the formula:

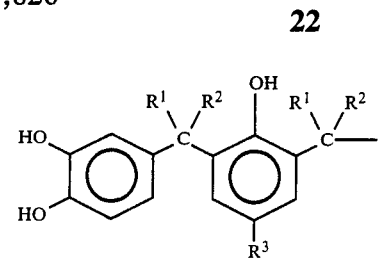

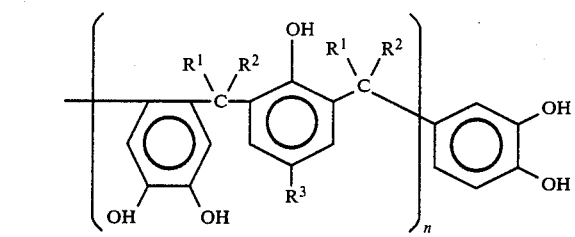

wherein $R^1$ and $R^2$ represents a hydrogen atom, $R^3$ represents $CH_3$, and n is 0, and wherein at least 80% of the phenolic hydroxyl groups are converted to glycidyl ether groups.

4. A polyepoxy compound consisting of a polyglycidyl ether of a polyhydric phenol of the formula:

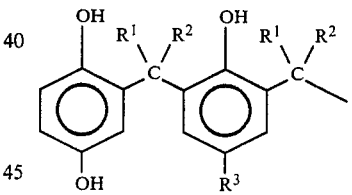

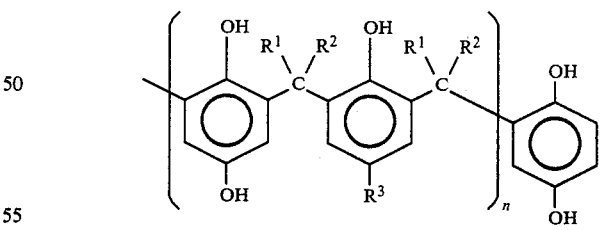

wherein $R^1$ and $R^2$ represent a hydrogen atom, $R^3$ represents $CH_3$, and n is 0, and wherein at least 80% of the phenolic hydroxyl groups are converted to glycidyl ether groups.

* * * * *